United States Patent [19]
Willms et al.

[11] Patent Number: 5,696,051
[45] Date of Patent: Dec. 9, 1997

[54] SYNERGISTIC HERBICIDE COMBINATIONS

[75] Inventors: Lothar Willms, Hillscheid; Klaus Bauer, Hanau; Hermann Bieringer, Eppstein/Ts; Erwin Hacker, Hochheim am Main, all of Germany

[73] Assignee: Hoechst Aktiengesellschaft, Frankfurt, Germany

[21] Appl. No.: 462,647

[22] Filed: Jun. 5, 1995

Related U.S. Application Data

[62] Division of Ser. No. 61,211, May 13, 1993, Pat. No. 5,461,019.

[30] Foreign Application Priority Data

May 15, 1992 [DE] Germany ............... 42 16 130.4

[51] Int. Cl.$^6$ ............... A01N 43/40; A01N 43/42; A01N 43/50; A01N 43/54
[52] U.S. Cl. ............... 504/130; 504/133; 504/134; 504/136
[58] Field of Search ............... 504/130, 133, 504/134, 136

[56] References Cited

U.S. PATENT DOCUMENTS

| | | | |
|---|---|---|---|
| 3,297,427 | 1/1967 | Richter | 504/144 |
| 4,638,068 | 1/1987 | Los | 504/191 |
| 4,749,404 | 6/1988 | Parsons | 504/247 |
| 5,030,271 | 7/1991 | Watkins | 504/130 |
| 5,256,625 | 10/1993 | Bussler et al. | 504/107 |

FOREIGN PATENT DOCUMENTS

| | | |
|---|---|---|
| A-0 181 628 | 5/1986 | European Pat. Off. . |
| A-0 190 666 | 8/1986 | European Pat. Off. . |
| A-0 485 207 | 5/1992 | European Pat. Off. . |
| A-0 496 608 | 7/1992 | European Pat. Off. . |
| A-0 524 394 | 1/1993 | European Pat. Off. . |
| A-0 525 474 | 2/1993 | European Pat. Off. . |
| 0492366 | 7/1993 | European Pat. Off. . |
| 0492367 | 7/1993 | European Pat. Off. . |
| A-2 584 265 | 1/1987 | France . |

OTHER PUBLICATIONS

Proceedings of the Western Society of Weed Science, Mar., 1991.

*Primary Examiner*—Richard L. Raymond
*Assistant Examiner*—Brian Bembenick
*Attorney, Agent, or Firm*—Curtis Morris & Safford P.C

[57] ABSTRACT

The invention relates to herbicidal compositions containing at least one compound from the group comprising imazaquin (A1), imazethapyr (A2) and imazethamethapyr (A3, AC 263222) in combination with at least one herbicide selected from the series comprising dicamba (B1), 2,4-D (B2), bromoxynil (B3), pyridate, the cyclohexanedione group and the pyridylsulfonylurea group.

14 Claims, No Drawings

SYNERGISTIC HERBICIDE COMBINATIONS

This application is a division of application Ser. No. 08/061,211, filed May 13, 1993, (U.S. Pat. No. 5,461,019).

The imidazolinones are a relatively new substance class of herbicidal active compounds, which are employed in various cultivated plant crops for selective weed control. These include herbicides such as imazaquin, imazethapyr and imazethamethapyr (AC 263222), which are employed, in particular, in soybeans.

Recently, however, it has also been possible to employ these herbicides in corn. On the one hand, because resistant corn species have been developed and on the other hand, because new safener active compounds have been found which enable selective use in corn crops (P 4041120.6 and P 4041121.4).

In biological tests of the use possibilities in corn, it has surprisingly been found that some mixtures of imidazolinones with other selective corn herbicides show unusual synergistic properties which are associated with great economic advantages.

By utilizing such synergistic effects, the application rates of the mixture components involved can be considerably reduced, and it is possible to control a wide spectrum of monocotyledon and dicotyledon weeds in one operation. The reduction in the application amounts relates in particular to the imidazolinones, but also the combination components with regard to their specific activity.

The use of mixtures which produce synergistic effects is associated with great economic, but also ecological, advantages.

Synergism is understood as meaning the mutual reinforcing action of two or more substances. In the present case, the combined use of the herbicides makes it possible that the application rates of the herbicides can be reduced and in spite of this the same herbicidal action is achieved, or that with the same application rates of the herbicides a greater action than that to be expected from the active compounds individually employed is achieved (synergistic effect).

The following herbicides showed synergistic activity, in particular in dicotyledon weeds, as mixture components for additionally broadening the spectrum of action: dicamba, 2,4-D, bromoxynil, pyridate and herbicides of the cyclohexanedione, sulfonylurea and pyridylsulfonylurea type.

The present invention thus relates to herbicidal compositions containing at least one compound from the group comprising imazaquin (A1), imazethapyr (A2) and imazethamethapyr (A3, AC 263222) in combination with at least one herbicide selected from the series comprising dicamba (B1), 2,4-D (B2), bromoxynil (B3), pyridate, the cyclohexanedione group, the sulfonylurea group and the pyridylsulfonylurea group.

The invention relates in particular to the following herbicides as mixture components:

cyclohexanediones, such as, for example, ICI-051 (2-[2-chloro-4-(methylsulfonyl)benzoyl]-1,3-cyclohexanedione (chloromesulone, sulcotrione)), sulfonylureas, such as, for example, primisulfuron (B4), nicosulfuron (B5), DPX-E 9636=renriduron or rimsulfuron (B6), thifensulfuron, amidosulfuron (B7), pyridylsulfonylureas, as described, for example, in German Patent Applications P 4000503.8 and P 4030577.5:
3-(4,6-dimethoxypyrimidin-2-yl)-1-[3-(N-methylsulfonyl)-amino-2-pyridylsulfonyl]urea, (see EP-A 402 316) (B8),
3-(4,6-dimethoxy-pyrimidin-2-yl)-1-[3-(3-fluoropropylsulfonyl)-2-pyridylsulfonyl]urea,
3-(4,6-dimethoxy-pyrimidin-2-yl)-1-[3-(2-methoxyethylsulfonyl)-2-pyridylsulfonyl]urea,
3-(4,6-dimethoxypyrimidin-2-yl)-1-[3-allylsulfonyl-2-pyridylsulfonyl]urea, (see WO 91/15478 and EP-A-0 342 569),
methyl 3-chloro-5-(4,6-dimethorypyrimidin-2-yl-carbamoyl-sulfamoyl)-1-methylpyrazole-4-carboxylate (NC 319=MON 12000, see EP 282 613) and CGA 152005 (1-(4-methoxy-6-methyltriazin-2-yl)-3-[2-(3,3,3-trifluoropropyl)-phenylsulfonyl]urea,
and other sulfonylureas and mixtures of various abovementioned sulfonylureas with one another, such as, for example, a mixture of nicosulfuron and DPX-E 9636.

Suitable mixture components are also other herbicides which, like sulfonylureas, inhibit the enzyme acetolactate synthase (ALS), for example substituted pyrimidines, such as, for example, 2-(2-benzyloxycarbonylpyrid-3-yloxy)-4,6-dimethoxypyrimidine (B9), and triazines, herbicidal sulfonamides, such as, for example, flumetsulam or triazolopyrimidinesulfonamides (Cordes, R. C. et al., Abstr. Meet. Weed Sci. Soc. Am. 31, 10, 1991, Percival, A., Pestic. Sci. 31,568, 1991), or other related compounds and mixtures of such active compounds with one another.

The abovementioned herbicides are described in the Pesticide Manual (Brit. Crop Prot. Council, 9th edition (1991) and in Weed Techn. (1991, Volume 5).

The application rates of the herbicides are in general between 0.01 and 2 kg/ha, i.e. the total amount of active compound combination to be applied is about 0.02 to 2 kg/ha. The required application rate can vary depending on the external conditions such as temperature and humidity, inter alia, and it is preferably between 0.05 and 1 kg/ha. The mixture ratios can vary within wide limits depending on the external conditions. A quantitative ratio between 1:20 and 20:1 is preferably selected.

These synergistic effects are achieved both in the case of mixtures with imazethapyr and in the case of application with other imidazolinones. A combination of the active compounds means that the herbicidal active compounds are applied together or one is applied a few days after the other as a so-called split application. In each case, the weeds react with increased sensitivity, such that a very good control can be achieved with the use of relatively low application rates.

In the following examples, the invention is illustrated in greater detail without being restricted thereto. Percentage details relate to the weight, if no other details are given.

The herbicides mentioned can be employed either as tank mixes, where each active compound is individually formulated and only mixed with other formulated herbicides in the spraying tank of the spray equipment at the time of application, or they can already be jointly formulated, namely in various ways, depending on which biological and/or physicochemical parameters are prespecified. Suitable formulation possibilities are, for example: wettable powders (WP), emulsifiable concentrates (EC), water-soluble powders (SP), water-soluble concentrates (SL), concentrated emulsions (EW) such as oil-in-water and water-in-oil emulsions, sprayable solutions or emulsions, capsule suspensions (CS), dispersions on an oil or water basis (SC), suspoemulsions, suspension concentrates, dusts (DP), oil-miscible solutions (OL), dressing agents, granules (GR) in the form of microgranules, spray granules, coated granules and adsorption granules, granules for application to the soil or by scattering, water-soluble granules (SG), water-dispersible granules (WG), ULV formulations, microcapsules and waxes.

These individual formulation types are known in principle and are described, for example, in: Winnacker-Küchler, "Chemische Technologie" Volume 7, C. Hauser Verlag Munich, 4th Edition 1986; Wade van Valkenburg, "Pesticide Formulations", Marcel Dekker N.Y., 1973; K. Martens, "Spray Drying Handbook", 3rd Edition 1979, G. Goodwin Ltd. London.

The required formulation auxiliaries such as inert materials, surfactants, solvents and other additives are also known and are described, for example, in: Watkins, "Handbook of Insecticide Dust Diluents and Carriers", 2nd Edition, Darland Books, Caldwell N.J.; H. v. Olphen "Instruction to Clay Colloid Chemistry", 2nd Edition, J. Wiley & Sons, N.Y., Marsden "Solvents Guide", 2nd Edition, Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", Wiss. Verlagsgesell., Stuttgart 1976; Winnacker-Küchler "Chemische Technologie", Volume 7, C. Hauser Verlag Munich, 4th Edition 1986.

Based on these formulations, combinations with other pesticidal substances, fertilizers and/or growth regulators can also be prepared, for example in the form of a finished formulation or as a tank mix.

Wettable powders are preparations which are uniformly dispersible in water, which apart from a diluent or inert substance additionally contain wetting agents, for example polyoxyethylated alkylphenols, polyoxyethylated fatty alcohols and fatty amines, fatty alcohol polyglycol ether sulfates, alkanesulfonates or alkylarylsulfonates and dispersing agents, for example sodium ligninsulfonate, sodium 2,2-dinaphthylmethane-6,6'-disulfonate, sodium dibutylnaphthalenesulfonate or alternatively sodium oleylmethyltauride in addition to the active compound.

Emulsifiable concentrates are prepared by dissolving the active compound in an organic solvent, for example butanol, cyclohexanone, dimethylformamide, xylene or alternatively higher-boiling aromatics or hydrocarbons with the addition of one or more emulsifiers. Emulsifiers which can be used, for example, are: calcium alkylarylsulfonates such as Ca dodecylbenzenesulfonate or nonionic emulsifiers such as fatty acid polyglycol esters, alkylaryl polyglycol ethers, fatty alcohol polyglycol ethers, propylene oxide/ethylene oxide condensation products (for example block polymers), alkyl polyethers, sorbitan fatty acid esters, polyoxyethylene sorbitan fatty acid esters or polyoxyethylene sorbitol esters.

Dusts are obtained by grinding the active compound with finely divided solid substances, for example talc, natural clays, such as kaolin, bentonire and pyrophyllite, or diatomaceous earth.

Granules can either be prepared by spraying the active compound onto adsorptive, granulated inert material or by applying active compound concentrates by means of tackifiers, for example polyvinyl alcohol, sodium polyacrylates or alternatively mineral oils, to the surface of carrier substances such as sand, kaolinites or granulated inert material. Suitable active compounds can also be granulated in the manner customary for the preparation of fertilizer granules—if desired in a mixture with fertilizers.

The agrochemical preparations as a rule contain 0.1 to 99% by weight, in particular 0.1 to 95% by weight, of the active compound mixture and 1 to 99.9% by weight, in particular 5 to 99.8% by weight, of a solid or liquid additive and 0 to 25% by weight, in particular 0.1 to 25% by weight, of a surfactant.

The active compound concentration in wettable powders is, for example, about 10 to 90% by weight, the remainder consists of customary formulation constituents. In the case of emulsifiable concentrates, the active compound concentration is about 1 to 80% by weight of active compounds. Dust-like formulations contain about 1 to 20% by weight of active compounds, sprayable solutions about 0.2 to 20% by weight of active compounds. In the case of granules, such as water-dispersible granules, the active compound content depends partly on whether the active compound is liquid or solid. As a rule, the content in the case of water-dispersible granules is between 10 and 90% by weight. In addition, said active compound formulations optionally contain the tackifiers, wetting agents, dispersants, emulsifiers, penetrants, solvents, fillers or carriers which are customary in each case.

For application, the formulations, which are present in commercially available form, are optionally diluted in a customary manner, for example in the case of wettable powders, emulsifiable concentrates, dispersions and water-dispersible granules by means of water. Dust-like preparations, granules and sprayable solutions are customarily not diluted any more with further inert substances before application. Particularly good activities of the agents according to the invention can be achieved if, in addition to the surfactants contained in the formulations, further wetting agents are added in concentrations from 0.1 to 0.5% by weight in the tank mix process, for example nonionic wetting agents or wetting agents of the fatty alcohol polyether sulfate type (see, for example, German Patent Application P 4029304.1).

The following examples serve to illustrate the invention:

Formulation Examples:

a) A dust is obtained by mixing 10 parts by weight of a compound of the imidazolinone type and one or more mixture components, and 90 parts by weight of talc as inert substance and comminuting in a hammer mill.

b) A readily water-dispersible, wettable powder is obtained by mixing 25 parts by weight of a compound of the imidazolinone type and one or more combination components, 64 parts by weight of kaolin-containing quartz as inert substance, 10 parts by weight of potassium ligninsulfonate and 1 part by weight of sodium oleoylmethyltaurate as wetting and dispersing agent and grinding in a pinned disk mill.

c) A readily water-dispersible dispersion concentrate is obtained by mixing 20 parts by weight of a compound of the imidazolinone type and one or more combination components, 6 parts by weight of alkylphenol polyglycol ether (Triton®×207), 3 parts by weight of isotridecanol polyglycol ether (8 EO) and 71 parts by weight of paraffinic mineral oil (boiling range, for example, about 255 to above 277° C.) and grinding in a ball mill to a fineness of less than 5 microns.

d) An emulsifiable concentrate is obtained from 15 parts by weight of a compound of the imidazolinone type and one or more combination components, 75 parts by weight of cyclohexanone as solvent and 10 parts by weight of ethoxylated nonylphenol as emulsifier.

e) Water-dispersible granules are obtained by mixing 75 parts by weight of a compound of the imidazolinone type and one or more combination components, 10 parts by weight of calcium ligninsulfonate,
5 parts by weight of sodium lauryl sulfate,
3 parts by weight of polyvinyl alcohol and
7 parts by weight of kaolin grinding in a pinned disk mill and granulating the powder in a fluidized bed by spraying on water as the granulating liquid.

f) Water-dispersible granules are also obtained by homogenizing and precomminuting 25 parts by weight of a compound of the imidazolinone type and one or more combination components, 5 parts by weight of sodium 2,2'-dinaphthylmethane-6,6-disulfonate,
2 parts by weight of sodium oleoylmethyltaurate,
1 parts by weight of polyvinyl alcohol,
17 parts by weight of calcium carbonate and
15 parts by weight of water in a colloid mill, then grinding in a bead mill and atomizing the suspension thus obtained in a spray tower by means of a single-substance nozzle and drying.

Biological Examples

Biological tests with various combinations of imazethapyr or other imidazolinones and herbicides which are also selectively employed in corn were carried out both in the greenhouse and under practical conditions in the open. In this connection, to improve the selectivity in corn, safeners were also employed, such as are disclosed in P 4041120.6 and P 4041121.4, in order to be able to apply the imidazolinones without damage to the corn crop. P 4141247.8 discloses that the safener active compounds used also prevent damage which is caused by mixtures of various herbicides, i.e. the safener active compounds applied protect the corn from damage by various active compound combinations, as were tested here.

The biological tests comprised a wide spectrum of various weeds and weed grasses, in particular those which are of great economical importance in corn cultivation. The treatment of the weeds here is carried out mainly post-emergence. The results were very surprising over a wide area. It was found, namely, that numerous combinations of imidazolinones, such as, for example, imazethapyr, display marked synergistic activity with various corn herbicides, i.e. the effectiveness found in practice is distinctly higher than the additive action which is to be expected on the basis of the observed action of the individual components when used alone.

Use Example

The crop plants, weeds and weed grasses were grown in the open or in a greenhouse in plastic pots up to the 4- or 5-leaf stage (see below) and then treated with compounds according to the invention post-emergence. The herbicides were applied here in the form of aqueous suspensions or emulsions using a water application rate, after conversion, of 300 l/ha. 4 weeks after treatment, the plants were assessed visually for any type of damage due to the applied herbicides, the extent of the prolonged inhibition of growth being taken into account. Assessment was in percentage values in comparison to untreated controls.

The herbicides employed according to the invention in the form of the mixtures employed show substantially better activities than would be expected on the basis of the individual action. The herbicide combinations thus act synergistically.

In the following, some results from the large number of tests carried out are presented, though without it being possible to restrict the demonstration of the synergistic activity only to these examples. To be more precise, unexpectedly good effectiveness was observed in numerous combinations, which extends above and beyond the expected additive action and may therefore be called synergistic.

The products were applied post-emergence in the following stage of growth:

| | | | |
|---|---|---|---|
| ECCR = *Echinochloa crus galli* | 3 leaves | 8–10 cm high |
| SEPU = *Setaria viridis* | 3–4 leaves | 7–9 cm high |
| PAMI = *Panicum miliaceum* | 3 leaves | 5–6 cm high |
| DISA = *Digitaria sanquinalis* | 3 leaves | 7–8 cm high |
| DAST - *Datura stramonium* | 2–3 lateral shoots | 7–8 cm high |
| CHAL - *Chenopodium album* | 3 lateral shoots | 3–4 cm high |

The temperatures in the greenhouse during the day were 20° to 22° C. and at night 16° to 18° C. 2 repetitions were carried out.

The results show that combinations of imazethapyr and sulfonylurea derivatives have synergistic activity in a wide area.

TABLE 1

| | g As/ha | ECCR | SEPU | PAMI |
|---|---|---|---|---|
| A2 | 25 | 97 | 97 | 75 |
| | 12.5 | 70 | 94 | 50 |
| | 6 | 45 | 85 | 40 |
| B1 | 500 | 20 | 0 | 10 |
| | 250 | 10 | 0 | 0 |
| | 125 | 0 | 0 | 0 |
| | 62.6 | 0 | 0 | 0 |
| B2 | 500 | 50 | 45 | 50 |
| | 250 | 15 | 20 | 30 |
| | 125 | 5 | 10 | 10 |
| | 63 | 0 | 0 | 0 |
| B3 | 500 | 0 | 20 | 45 |
| | 250 | 0 | 10 | 30 |
| | 125 | 0 | 0 | 10 |
| | 62.5 | 0 | 0 | 0 |
| B7 | 12 | 10 | 20 | 25 |
| | 6 | 0 | 20 | 10 |
| B8 | 12 | 80 | 80 | 65 |
| | 6 | 70 | 70 | 60 |
| | 3 | 65 | 60 | 50 |
| B9 | 100 | 45 | 99 | 97 |
| | 50 | 30 | 97 | 95 |
| | 25 | 10 | 93 | 85 |
| | 12.5 | 0 | 80 | 80 |
| A2 + B1 | 25 + 125 | 99 (97) | 100 (97) | 85 (75) |
| | 12.5 + 125 | 97 (70) | 100 (94) | 85 (50) |
| | 6 + 126 | 75 (45) | 97 (85) | 70 (40) |
| | 25 + 62.5 | 99 (97) | 99 (97) | 93 (75) |
| | 12.5 + 62.5 | 97 (70) | 99 (94) | 75 (50) |
| | 6 + 62.5 | 80 (45) | 95 (85) | 45 (40) |
| A2 + B2 | 25 + 125 | 95 (97) | 100 (97) | 97 (77) |
| | 12.5 + 125 | 93 (71) | 99 (94) | 94 (55) |
| | 6 + 126 | 90 (48) | 98 (86) | 75 (46) |
| | 25 + 62.5 | 95 (97) | 100 (97) | 93 (75) |
| | 12.5 + 62.5 | 85 (70) | 99 (94) | 80 (50) |
| | 6 + 62.5 | 75 (45) | 97 (85) | 80 (40) |
| A2 + B3 | 25 + 125 | 100 (97) | 99 (97) | 75 (77) |
| | 12.5 + 125 | 85 (70) | 85 (94) | 75 (55) |
| | 6 + 125 | 70 (45) | 70 (85) | 45 (46) |
| | 25 + 62.5 | 95 (97) | 98 (97) | 55 (75) |
| | 12.5 + 62.5 | 80 (70) | 93 (94) | 50 (50) |
| | 6 + 62.5 | 60 (45) | 75 (85) | 45 (40) |

TABLE 1-continued

|  | g As/ha | ECCR | SEPU | PAMI |
|---|---|---|---|---|
| A2 + B7 | 12 + 6 | 80 (70) | 90 (95) | 65 (55) |
| A2 + B8 | 25 + 3 | 89 (99) | 88 (98) | 90 (86) |
|  | 12 + 3 | 84 (88) | 85 (98) | 86 (75) |
| A2 + B9 | 25 + 25 | 100 (97) | 100 (100) | 100 (96) |
|  | 12 + 25 | 98 (73) | 98 (100) | 100 (92) |
|  | 6 + 25 | 97 (50) | 85 (99) | 94 (91) |
|  | 25 + 12.5 | 97 (97) | 100 (99) | 97 (95) |
|  | 12.5 + 12.5 | 93 (70) | 95 (99) | 95 (90) |
|  | 0 + 12.5 | 85 (45) | 80 (97) | 93 (88) |

B9: 2-(2-Benzyloxycarbonylpyrid-3-yloxy)-4,6-dimethoxypyrimidine

TABLE 2

Activity of the herbicides and herbicide mixtures against various grasses and weeds in %.

|  | g AS/ha | ECCR | SEPU | PAMI | DISA | DAST | CHAL |
|---|---|---|---|---|---|---|---|
| A2 | 25 | 70 | 95 | 80 | 85 | 80 | 80 |
|  | 12.5 | 60 | 80 | 65 | 80 | 60 | 60 |
|  | 6.25 | 20 | 60 | 50 | 50 | 40 | 35 |
|  | 3.12 | 0 | 35 | 30 | 0 | 30 | 5 |
| B4 | 50 | 30 | 50 | 75 | 30 | 90 | 98 |
|  | 25 | 10 | 30 | 40 | 10 | 65 | 97 |
|  | 12.5 | 0 | 10 | 15 | 0 | 60 | 94 |
|  | 6.25 | 0 | 0 | 0 | 0 | 50 | 90 |
|  | 3.12 | 0 | 0 | 0 | 0 | 40 | 85 |
| B5 | 12.5 | 90 | 90 | 93 | 60 | 50 | 75 |
|  | 6.25 | 65 | 70 | 85 | 40 | 40 | 60 |
|  | 3.12 | 15 | 40 | 50 | 0 | 25 | 40 |
| B6 | 3.12 | 70 | 90 | 93 | 30 | 0 | 75 |
|  | 1.6 | 0 | 30 | 70 | 0 | 0 | 60 |
| B8 | 12.5 | 93 | 93 | 70 | 75 | 50 | 98 |
|  | 6.25 | 70 | 50 | 40 | 35 | 40 | 95 |
|  | 3.12 | 40 | 15 | 0 | 0 | 30 | 85 |
| A2 + B4 | 12.5 + 6.25 | 75 (60) | 97 (80) | 93 (65) | 75 (80) | 70 (80) | 95 (96) |
|  | 6.25 + 3.12 | 55 (20) | 95 (60) | 65 (50) | 65 (50) | 70 (66) | 90 (90) |
|  | 3.12 + 1.6 | 10 (0) | 75 (35) | 15 (30) | 45 (0) | 65 (58) | 80 (86) |
| A2 + B5 | 12.5 + 3.12 | 93 (64) | 97 (88) | 99 (82) | 95 (80) | 90 (70) | 95 (76) |
|  | 6.25 + 1.6 | 90 (32) | 95 (76) | 97 (75) | 90 (50) | 70 (55) | 95 (61) |
|  | 3.12 + 0.8 | 80 (15) | 95 (61) | 88 (65) | 70 (0) | 60 (48) | 80 (43) |
|  | 6.25 + 0.8 | 70 (32) | 93 (76) | 90 (75) | 90 (50) | 50 (55) | 85 (61) |
|  | 3.12 + 0.4 | 65 (15) | 90 (61) | 80 (65) | 80 (0) | 40 (48) | 70 (43) |
| A2 + B6 | 6.25 + 0.8 | 80 (20) | 95 (72) | 100 (85) | 70 (50) | 70 (40) | 85 (74) |
|  | 3.12 + 0.4 | 70 (0) | 85 (55) | 95 (79) | 55 (0) | 40 (0) | 75 (62) |
|  | 6.25 + 0.4 | 70 (20) | 90 (72) | 80 (85) | 80 (50) | 50 (40) | 80 (74) |
|  | 3.12 + 0.2 | 45 (0) | 70 (55) | 60 (79) | 45 (0) | 40 (0) | 70 (62) |
| A2 + B8 | 6.25 + 3.12 | 80 (52) | 93 (66) | 75 (50) | 97 (50) | 70 (58) | 95 (90) |
|  | 3.12 + 1.6 | 70 (40) | 85 (45) | 70 (30) | 90 (0) | 55 (51) | 88 (86) |

B8 = 3-(4,6-dimethoxypyrimidin-2-yl)-1-[3-(N-methy-N-methylsulfonylamino)-2-pyridylsulfonyl]urea (see page 3 of the application).

We claim:

1. An herbicidal agent containing at least one compound from the group consisting of imazaquin, imazethapyr and imazethamethapyr in combination with at least one herbicide selected from the group consisting of primisulfuron, nicosulfuron, rimsulfuron, amidosulfuron and the pyridylsulfonylureas.

2. An herbicidal agent as claimed in claim 1, which contains at least one compound selected from the group consisting of imazaquin, imazethapyr and imazethamethapyr in combination with primisulfuron.

3. An herbicidal agent as claimed in claim 1, which contains at least one compound selected from the group consisting of imazaquin, imazethapyr and imazethamethapyr in combination with nicosulfuron.

4. An herbicidal agent as claimed in claim 1, which contains at least one compound selected from the group consisting of imazaquin, imazethapyr and imazethamethapyr in combination with amidosulfuron.

5. An herbicidal agent as claimed in claim 1, which contains at least one compound selected from the group consisting of imazaquin, imazethapyr and imazethamethapyr in combination with a pyridylsulfonylurea.

6. An herbicidal agent which comprises imazethapyr, in combination with rimsulfuron.

7. An herbicidal agent as claimed in claim 1, wherein the pyridylsulfonylurea is selected from the group consisting of 3-(4,6-dimethoxypyrimidin-2-yl)-1-[3-(N-methylsulfonyl)-amino-2-pyridylsulfonyl]urea, 3-(4,6-dimethoxy-pyrimidin-2-yl)-1-[3-(3-fluoropropylsulfonyl)-2-pyridylsulfonyl]urea, 3-(4,6-dimethoxy-pyrimidin-2-yl)-1-[3-(2-methoxyethylsulfonyl)-2-pyridylsulfonyl]urea, 3-(4,6-dimethoxypyrimidin-2-yl)-1-[3-allylsulfonyl-2-pyridylsulfonyl]urea, methyl 3-chloro-5-(4,6-dimethoxypyrimidin-2-yl-carbamoyl-sulfamoyl)-1-methylpyrazole-4-carboxylate and (1-(4-methoxy-6-methyltriazin-2-yl)-3-[2-(3,3,3-trifluoropropyl)-phenylsulfonyl]urea.

8. An herbicidal agent as claimed in claim 1, wherein the pyridylsulfonylurea is 3-(4,6-dimethoxypyrimidin-2-yl)-1-[3-(N-methylsulfonyl)-amino-2-pyridylsulfonyl]urea.

9. An herbicidal agent containing at least one compound selected from the group consisting of imazaquin, imazethapyr and imazethamethapyr, in combination with rimsulfuron.

10. A method for the control of undesired plants, which comprises applying an herbicidally effective amount of a composition as claimed in claim 9, to the plants or to the cultivation areas.

11. A method for the control of undesired plants, which comprises applying an herbicidally effective amount of a composition as claimed in claim 1, to the plants or to the cultivation areas.

12. A method for the control of undesired plants, which comprises applying an herbicidally effective amount of a composition as claimed in claim 2, to the plants or to the cultivation areas.

13. A method for the control of undesired plants, which comprises applying an herbicidally effective amount of a composition as claimed in claim 3, to the plants or to the cultivation areas.

14. A method for the control of undesired plants, which comprises applying an herbicidally effective amount of a composition as claimed in claim 4, to the plants or to the cultivation area.

* * * * *